(12) United States Patent
Sutton et al.

(10) Patent No.: US 12,237,082 B2
(45) Date of Patent: Feb. 25, 2025

(54) CLINICAL TRIAL MATCHING SYSTEM USING INFERRED BIOMARKER STATUS

(71) Applicant: Flatiron Health, Inc., New York, NY (US)

(72) Inventors: Lauren Sutton, Cary, NC (US); David Light, San Francisco, CA (US); Claire Saint-Donat, New York, NY (US); Frank Chen, Forrest Hills, NY (US); Alexander Rich, New York, NY (US); Barry Leybovich, Basking Ridge, NJ (US); Prakrit Baruah, Providence, RI (US); Nisha Singh, Jamaica, NY (US); Forrest Xiao, New York, NY (US); Edward Liu, New York, NY (US)

(73) Assignee: Flatiron Health, Inc., New York, NY (US)

( * ) Notice: Subject to any disclaimer, the term of this patent is extended or adjusted under 35 U.S.C. 154(b) by 659 days.

(21) Appl. No.: 17/564,706

(22) Filed: Dec. 29, 2021

(65) Prior Publication Data
US 2022/0208376 A1 Jun. 30, 2022

Related U.S. Application Data

(60) Provisional application No. 63/133,084, filed on Dec. 31, 2020.

(51) Int. Cl.
*G16H 50/20* (2018.01)

(52) U.S. Cl.
CPC .................................. *G16H 50/20* (2018.01)

(58) Field of Classification Search
CPC ....................................................... G16H 50/20
(Continued)

(56) References Cited

U.S. PATENT DOCUMENTS 11,521,724 B2 * 12/2022 Das .......................... G16H 50/50
11,537,818 B2 * 12/2022 Nori ........................ G06F 18/214
(Continued)

OTHER PUBLICATIONS

International Search Report, issued from the European Patent Office in International Application No. PCT/US2019/058484, dated Jan. 21, 2020 (16 pages).

*Primary Examiner* — Reza Nabi
(74) *Attorney, Agent, or Firm* — Wolf, Greenfield & Sacks, P.C.

(57) ABSTRACT

A model-assisted system for identifying a group of patients for a cohort using a generalized biomarker model may include a processor programmed to provide, to a generalized biomarker model, a first biomarker associated with a cohort, the generalized biomarker model being trained based on one or more second biomarkers; receive, from the generalized biomarker model, an output indicating a plurality of individuals with associated likelihoods of at least one of: having an attribute associated with the third biomarker or having been tested for the attribute associated with the first biomarker; determine a likelihood threshold based on a predetermined cohort size associated with the first biomarker and identify, based on the output, a group of the plurality of individuals for inclusion in a cohort, each individual in the group of the plurality of individuals being associated with a likelihood received from the generalized biomarker model that satisfies the likelihood threshold.

20 Claims, 10 Drawing Sheets

(58) Field of Classification Search
USPC .......................................................... 705/2
See application file for complete search history.

(56) References Cited

U.S. PATENT DOCUMENTS

| | | | | |
|---|---|---|---|---|
| 11,538,583 | B2* | 12/2022 | Isobe | G16H 10/60 |
| 11,586,613 | B2* | 2/2023 | Korpman | G06F 16/9577 |
| 11,651,252 | B2* | 5/2023 | Haimson | G16H 50/30 |
| | | | | 705/3 |
| 11,694,777 | B2* | 7/2023 | Birnbaum | G16H 10/20 |
| | | | | 705/3 |
| 11,728,014 | B2* | 8/2023 | Rich | G16H 50/30 |
| | | | | 705/2 |
| 11,875,903 | B2* | 1/2024 | Schaeffer | G06Q 10/10 |
| 11,942,226 | B2* | 3/2024 | Bettencourt-Silva | |
| | | | | G16H 10/60 |
| 12,040,059 | B2* | 7/2024 | Bhattacharyya | G16H 40/20 |
| 12,051,488 | B2* | 7/2024 | Bhattacharyya | G06N 5/04 |
| 12,100,517 | B2* | 9/2024 | Birnbaum | G16H 50/50 |
| 2014/0122126 | A1* | 5/2014 | Riskin | G06F 40/30 |
| | | | | 705/3 |
| 2015/0242979 | A1* | 8/2015 | Abts | G06Q 50/2057 |
| | | | | 705/328 |
| 2016/0341729 | A1* | 11/2016 | Raftery | G01N 33/57419 |
| 2017/0091937 | A1* | 3/2017 | Barnes | G06V 10/806 |
| 2018/0068083 | A1* | 3/2018 | Cohen | G16H 10/60 |
| 2018/0300640 | A1* | 10/2018 | Birnbaum | G06N 5/046 |
| 2018/0330824 | A1* | 11/2018 | Athey | G16B 40/00 |
| 2020/0234800 | A1* | 7/2020 | Will | G16H 10/20 |
| 2020/0237452 | A1* | 7/2020 | Wolf | G06F 3/048 |
| 2020/0243167 | A1* | 7/2020 | Will | G06N 20/20 |
| 2021/0257106 | A1* | 8/2021 | Birnbaum | G06F 16/35 |
| 2021/0310077 | A1* | 10/2021 | Yoshimoto | C12Q 1/6886 |
| 2022/0208376 | A1* | 6/2022 | Sutton | G16H 10/20 |
| 2022/0284999 | A1* | 9/2022 | Rich | G06F 16/3346 |
| 2023/0197218 | A1* | 6/2023 | Gnanasambandam | |
| | | | | G16H 10/60 |
| | | | | 705/3 |
| 2023/0197220 | A1* | 6/2023 | Blarre | G16H 10/60 |
| | | | | 705/3 |
| 2024/0105333 | A1* | 3/2024 | Van Der Zaag | G16B 20/20 |
| 2024/0257941 | A1* | 8/2024 | Mason | G16H 20/30 |

* cited by examiner

≡  Trials  Patients  Feasibility  Reports                    🔍 Search

2. Clinical Profile
Selections, excluding lines of therapy, will be used as inclusion criteria for patient matching.

Cohort Name

[                    ] — 610

Patient Matching Status — 620
● On  ○ Off

Trial Diseases — 630                ☐ No disease for trial
[ Select trial diseases ...        ▸ ]

Metastatic Status — 640
○ Metastatic Only   ○ Non-metastatic Only
● Either Metastatic or Non-metastatic

Lines of Therapy — 650
[ All lines of therapy            ▸ ]

FIG. 6

CLINICAL TRIAL MATCHING SYSTEM USING INFERRED BIOMARKER STATUS

CROSS REFERENCE TO RELATED APPLICATION

This application is based on and claims the benefit of priority of U.S. Provisional Application No. 63/133,084, filed on Dec. 31, 2020. The contents of the foregoing application are incorporated herein by reference in their entirety.

BACKGROUND

Technical Field

The present disclosure relates to the selection of cohorts and, more specifically, to the use of one or more generalized models to automatically select cohorts.

Background Information

In cancer treatment and in the treatment of various other diseases, there is an increasing drive to provide personalized treatment for patients. As one example, in order to provide a more effective treatment, patients with a particular form of cancer (e.g., lung cancer breast cancer, etc.) may be provided an individualized treatment plan based on genomic markers of the individual's tumor cells. Each of the tumor cells may have a particular genetic profile defining how they interact with other cells in the body and defining the kinds of biological pathways that may allow for the most effective treatment.

Thus, as the medical industry moves towards more individualized treatment plans, it may be increasingly important to be able to identify patients having certain treatment histories and/or characteristics. Returning to the example of oncology patients, it may be desirable to identify patients exhibiting certain biomarkers. For example, patients may be identified as candidates for particular treatments, particular clinical trials, or other similar groups based on whether they have been tested for a particular biomarker and the results of the treatment. However, identifying patients with particular biomarkers may be difficult when examining large groups of medical data. For example, this may require searching through thousands of medical records for an indication of whether a patient has been tested for a biomarker and to find the result of the tests. Complicating matters further, individual patients are often tested for hundreds of different biomarkers, many of which are not used as a basis for treatment of the patient. In addition, the medical records often contain handwritten notes or other text which may make automation of this process more difficult. Some solutions may include developing a machine learning model to determine whether a patient has been tested for a specific biomarker. For example, the model may be trained based on a set of medical records where it is known whether the patient has been tested for a particular biomarker or not. But such solutions require individualized models for each biomarker, which may not be feasible due to the wide variety of biomarkers that may be tested for and the limited data available for certain biomarkers.

Thus, there is a need for an improved approach for identifying patients having particular treatment characteristics. Solutions should allow for development of a machine learning model that is not dependent on the particular biomarkers (or other characteristics) that were used to train the model. Accordingly, using a generalized biomarker model, patients associated with a particular biomarker may be identified, regardless of the availability of medical data associated with that particular biomarker.

SUMMARY

Embodiments consistent with the present disclosure include systems and methods for identifying candidates associated with a particular biomarker. In an embodiment, a model-assisted system may comprise a least one processor. The processor may be programmed to provide, to a generalized biomarker model, a first biomarker associated with a cohort, the generalized biomarker model being trained based on one or more second biomarkers to detect one or more documents associated with representations of a biomarker or biomarker testing, wherein the first biomarker is different from the one or more second biomarkers; receive, from the generalized biomarker model, an output indicating a plurality of individuals with associated likelihoods of at least one of having an attribute associated with the first biomarker or having been tested for the attribute associated with the first biomarker; determine a likelihood threshold based on a predetermined cohort size associated with the first biomarker; and identify, based on the output, a group of the plurality of individuals for inclusion in a cohort, each individual in the group of the plurality of individuals being associated with a likelihood received from the generalized biomarker model that satisfies the likelihood threshold.

In an embodiment, a method for identifying a group of patients for a cohort using a generalized biomarker model is disclosed. The method may include providing, to the generalized biomarker model, a first biomarker associated with a cohort, the generalized biomarker model being trained based on one or more second biomarkers to detect one or more documents associated with representations of a biomarker or biomarker testing, wherein the first biomarker is different from the one or more second biomarkers; receiving, from the generalized biomarker model, an output indicating a plurality of individuals with associated likelihoods of at least one of having an attribute associated with the first biomarker or having been tested for the attribute associated with the first biomarker; determining a likelihood threshold based on a predetermined cohort size associated with the first biomarker, and identifying, based on the output, a group of the plurality of individuals for inclusion in a cohort, each individual in the group of the plurality of individuals being associated with a likelihood received from the generalized biomarker model that satisfies the likelihood threshold.

Consistent with other disclosed embodiments, non-transitory computer readable storage media may store program instructions, which are executed by at least one processing device and perform any of the methods described herein.

BRIEF DESCRIPTION OF THE DRAWINGS

The accompanying drawings, which are incorporated in and constitute part of this specification, and together with the description, illustrate and serve to explain the principles of various exemplary embodiments. In the drawings:

FIG. 6 illustrates an example user interface for selecting patients for a clinical trial, consistent with the disclosed embodiments.

DETAILED DESCRIPTION

Figure 1:
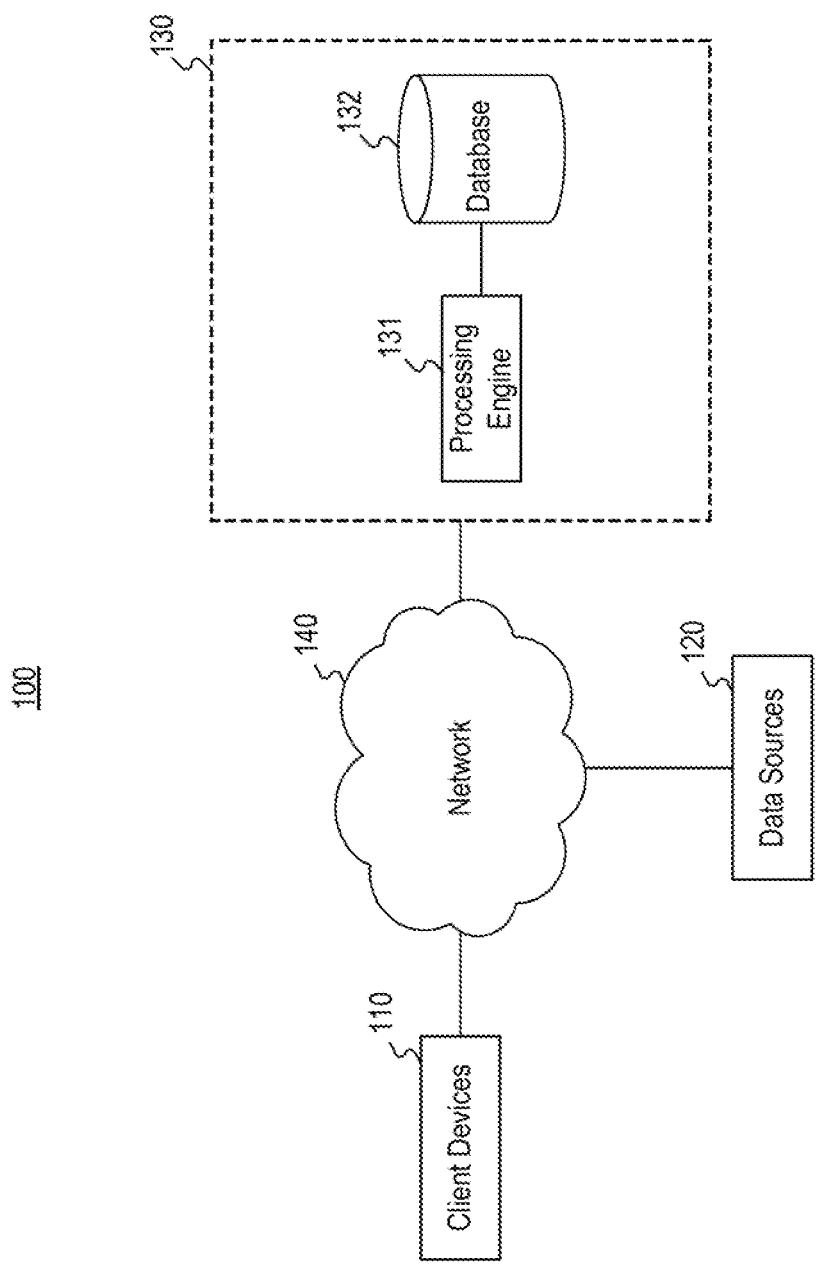
FIG. 1 is a block diagram illustrating an exemplary system environment for implementing embodiments consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, nonvolatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

Embodiments of the present disclosure provide systems and methods for identifying patients based on a generalized model. A user of the disclosed systems and methods may encompass any individual who may wish to access and/or analyze patient data and/or perform an experiment using a selected cohort of patients. Thus, throughout this disclosure, references to a "user" of the disclosed systems and methods may encompass any individual, such as a physician, a researcher, a quality assurance department at a health care institution, and/or any other individual. A generalized biomarker model is described in U S Published Patent Application No. 2021/0257106 A1, the contents of which are incorporate herein by reference in its entirety.

FIG. 1 illustrates an exemplary system environment 100 for implementing embodiments consistent with the present disclosure, described in detail below. As shown in FIG. 1, system environment 100 includes several components, including client devices 110, data sources 120, system 130, and/or network 140. It will be appreciated from this disclosure that the number and arrangement of these components is exemplary and provided for purposes of illustration. Other arrangements and numbers of components may be used without departing from the teachings and embodiments of the present disclosure.

As shown in FIG. 1, exemplary system environment 100 includes a system 130. System 130 may include one or more server systems, databases, and/or computing systems configured to receive information from entities over a network, process the information, store the information, and display/transmit the information to other entities over the network. Thus, in some embodiments, the network may facilitate cloud sharing, storage, and/or computing. In one embodiment, system 130 may include a processing engine 131 and one or more databases 132, which are illustrated in a region bounded by a dashed line representing system 130 in FIG. 1. Processing engine 140 may comprise at least one processing device, such as one or more generic processors, e.g., a central processing unit (CPU), a graphics processing unit (GPU), or the like and/or one or more specialized processors, e.g., an application-specific integrated circuit (ASIC), a field-programmable gate array (FPGA), or the like.

The components of environment 100 (including system 130, client devices 110, and data sources 120) may communicate with each other or with other components through a network 140. Network 140 may comprise various types of networks, such as the Internet, a wired Wide Area Network (WAN), a wired Local Area Network (LAN), a wireless WAN (e.g., WiMAX), a wireless LAN (e.g., IEEE 802.11, etc.), a mesh network, a mobile/cellular network, an enterprise or private data network, a storage area network, a virtual private network using a public network, a nearfield communications technique (e.g., Bluetooth, infrared, etc.), or various other types of network communications. In some embodiments, the communications may take place across two or more of these forms of networks and protocols.

System 130 may be configured to identify patients based on particular properties or characteristics associated with the patient and/or a treatment received by the patient. In some embodiments, the characteristics may be based on particular biomarkers. For example, system 130 may be configured to identify patients based on whether they have been tested for a specific biomarker, specific test results or other attributes associated with the biomarker (having been tested positive, negative, etc.), or various other characteristics. While patient selection based on biomarkers or biomarker status is used throughout the present disclosure, it is understood that the disclosed systems, methods, and/or techniques may similarly be used for other means of identifying patients (e.g., whether a patient has been prescribed a particular drug, whether the patient has received a particular treatment, etc.). Similarly, it is understood that in other embodiments, the disclosed systems, methods, and/or techniques may similarly be used for identifying other individuals, objects, entities, etc. based on a generalized model.

System 130 may be configured to receive patient medical information and other information from data sources 120 or other sources in network 140. In some embodiments, the medical information may be stored in the form of one or more medical records, each medical record being associated with a patient. More specifically, system 130 may be configured to receive and store the data transmitted over a network 140 from various data sources, including data sources 120, process the received data, and transmit data and results based on the processing to client device 110. Data sources 120 may include a variety of sources of medical information for a patient. For example, data sources 120 may include medical care providers of the patient, such as physicians, nurses, specialists, consultants, hospitals, clinics, and the like. Data sources 120 may also include laboratories such as radiology or other imaging labs, hematology labs, pathology labs, etc. Data sources 120 may also include insurance companies or any other sources of patient data.

System 130 may be configured to develop and use one or more models to identify patients having particular characteristics based on the medical records. For example, system 130 may use machine learning techniques to develop a model based on training data. In some embodiments, system 130 may develop generalized models, which may be trained on a specific set of characteristics or properties, but that may be used more generally to identify patients having other characteristics that may be treated similarly in patient medical records. For example, where system 130 is used to identify patients associated with a particular biomarker, system 130 may develop or implement a generalized biomarker model. While it may be desirable to have separate models developed for each biomarker, this may not be feasible. For example, while some biomarkers may be commonly tested for in a wide group of patients, others may be tested relatively infrequently on a small sample of patients. Accordingly, it may be feasible to develop specific biomarker models for the more common biomarkers where sample data is readily available, but may be too difficult or costly to develop specific biomarkers for all biomarkers due to the vast amount of biomarkers that may be tested for and the limited data set that may be available for some biomarkers.

Thus, a generalized biomarker model may be developed, which may be trained using one or more biomarkers included in a first set. The first set of biomarkers may be biomarkers for which sufficient information is available within medical records or other data to develop an accurate or reliable machine learning model. Because medical records may describe and/or discuss many biomarkers in similar ways (e.g., with similar structure, using common words, etc.), the generalized biomarker model may be used for biomarkers other than those included in the first set. For example, physicians describing test results for a common biomarker (e.g., one included in the first set), may describe test results associated with other biomarkers in a similar way. As a result, the generalized biomarker model may be configured to identify not only patients that have been tested for the first set of biomarkers, but patients that have been tested for biomarkers other than those in the first set. System 130 may apply the one or more generalized models to the received medical results to identify patients associated with a particular characteristic (e.g., having been tested for a particular biomarker, having tested positive for a particular biomarker, etc.). The use of the generalized biomarker model may provide more accurate results than merely performing a text search for a given biomarker identifier. For example, physicians' notes including "hold off on testing for EGFR" may indicate the patient has not been tested for the EGFR biomarker, but the results would still come up in a text search. It is understood that this is an example, and more complex relationships between the biomarker and the surrounding text may occur. While the generalized model is described with reference to biomarkers, it is understood that this is provided by way of example, and generalized models may be developed for identifying patients based on other characteristics (e.g., prescribed drugs, prescribed treatments, other forms of tests, etc.). Further, the generalized biomarker model may be used not only for determining whether patients exhibit a particular attribute associated with a biomarker (e.g., positive/negative result, changes over time, etc.) but also whether patients have been tested for the attribute. Accordingly, any reference throughout the present disclosure to determinations whether a patient has an attribute may equally apply to determinations whether the patient has been tested for the attribute, and vice versa.

System 130 may further communicate with one or more client devices 110 over network 140. For example, system 130 may provide results based on analysis of information from data sources 120 to client device 110. Client device 110 may include any entity or device capable of receiving or transmitting data over network 140. For example, client device 110 may include a computing device, such as a server or a desktop or laptop computer. Client device 110 may also include other devices, such as a mobile device, a tablet, a wearable device (i.e., smart watches, implantable devices, fitness trackers, etc.), a virtual machine, an IoT device, or other various technologies. In some embodiments, client device 110 may transmit queries for information about one or more patients over network 140 to system 130, such as a query for patients having been tested for a particular biomarker, or various other information about a patient.

In some embodiments, system 130 may be configured to select one or more cohorts. As used herein, a cohort may include any grouping of information (people, articles, objects, etc.) that shares at least one common characteristic or that exhibit attributes meeting a predefined set of criteria. In some embodiments, a cohort may include individuals that exhibit at least one common characteristic from a medical perspective e.g., demographic or clinical characteristics). An individual may include any member of one or more groups (e.g., objects, people, articles, etc.). For example, those individuals from a population determined to have a certain type of disease, or more specifically, having been tested for certain biomarkers associated with that disease may be identified and placed in a common cohort. Cohorts may be assembled for various purposes. In some instances, cohorts may be assembled to form groups used to analyze the characteristics of certain diseases, such as their epidemiology, treatment approaches, how outcomes such as mortality or progression of disease depend on certain variables, or the like.

The various components of system environment 100 may include an assembly of hardware, software, and/or firmware, including a memory, a central processing unit (CPU), and/or user interface. Memory may include any type of RAM or ROM embodied in a physical storage medium, such as magnetic storage including floppy disk, hard disk, or magnetic tape; semiconductor storage such as solid-state disk (SSD) or flash memory; optical disc storage; or magneto-optical disc storage. A CPU may include one or more processors for processing data according to a set of programmable instructions or software stored in the memory. The functions of each processor may be provided by a single dedicated processor or by a plurality of processors. Moreover, processors may include, without limitation, digital signal processor (DSP) hardware, or any other hardware capable of executing software. An optional user interface may include any type or combination of input/output devices, such as a display monitor, keyboard, and/or mouse.

Data transmitted and/or exchanged within system environment 100 may occur over a data interface. As used herein, a data interface may include any boundary across which two or more components of system environment 100 exchange data. For example, environment 100 may exchange data between software, hardware, databases, devices, humans, or any combination of the foregoing. Furthermore, it will be appreciated that any suitable configuration of software, processors, data storage devices, and networks may be selected to implement the components of system environment 100 and features of related embodiments.

Figure 2A:
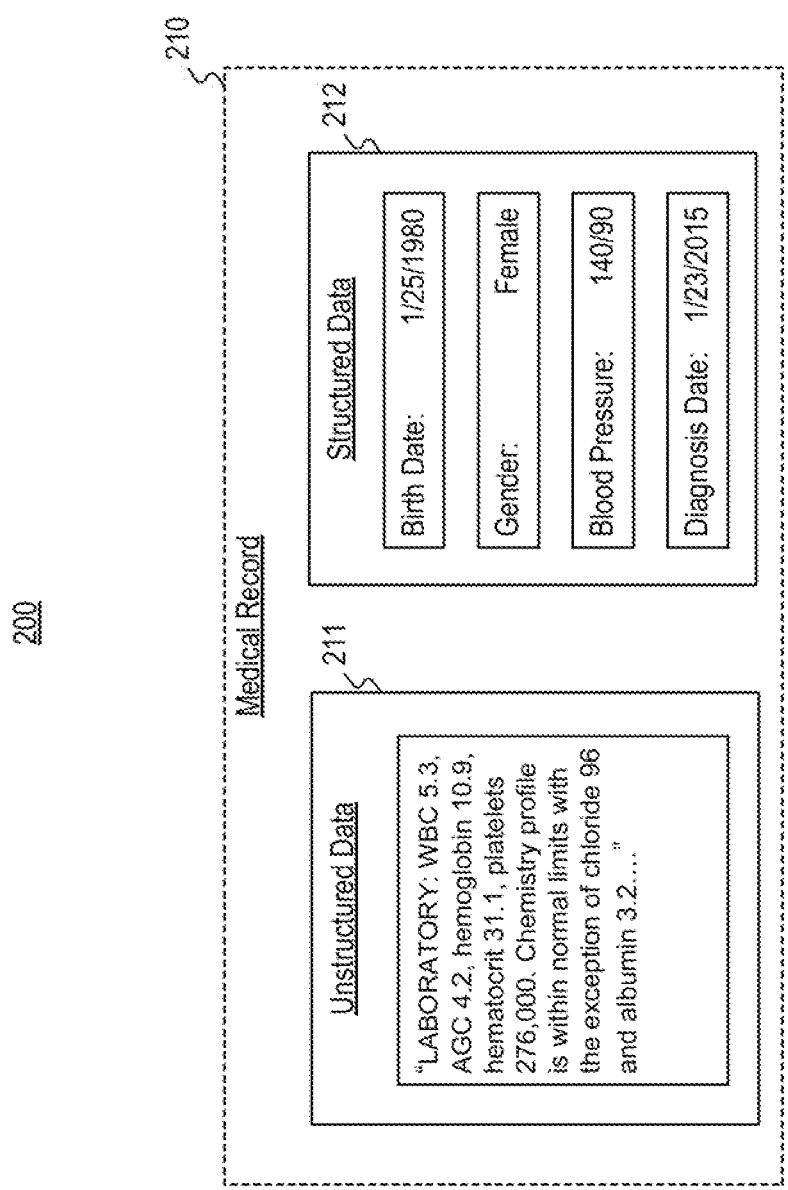
FIG. 2A is a block diagram illustrating an exemplary medical record for a patient consistent with the present disclosure.

FIG. 2 illustrates an exemplary medical record 200 for a patient. Medical record 200 may be received from data sources 120 and processed by system 130 to identify patients as described above. The records received from data sources 120 (or elsewhere) may include both structured data 210 and unstructured data 220, as shown in FIG. 2. Structured data 210 may include quantifiable or classifiable data about the patient, such as gender, age, race, weight, vital signs, lab results, date of diagnosis, diagnosis type, disease staging (e.g., billing codes), therapy timing, procedures performed, visit date, practice type, insurance carrier and start date, medication orders, medication administrations, or any other measurable data about the patient. Unstructured data may include information about the patient that is not quantifiable or easily classified, such as physician's notes or the patient's lab reports. Unstructured data 220 may include information such as a physician's description of a treatment plan, notes describing what happened at a visit, descriptions of how patient is doing, radiology reports, pathology reports, etc. In some embodiments, the unstructured data may include data associated with one or more biomarkers. For example, the unstructured data may include notes (e.g., from a physician, a nurse, a lab technician, etc.) discussing test results associated with a particular biomarker (e.g., whether the patient has been tested, results of the test, analysis of the results, etc.).

In the data received from data sources 120, each patient may be represented by one or more records generated by one or more health care professionals or by the patient. For example, a doctor associated with the patient, a nurse associated with the patient, a physical therapist associated with the patient, or the like, may each generate a medical record for the patient. In some embodiments, one or more records may be collated and/or stored in the same database. In other embodiments, one or more records may be distributed across a plurality of databases in some embodiments, the records may be stored and/or provided a plurality of electronic data representations. For example, the patient records may be represented as one or more electronic files, such as text files, portable document format (PDF) files, extensible markup language (XML) files, or the like. If the documents are stored as PDF files, images, or other files without text, the electronic data representations may also include text associated with the documents derived from an optical character recognition process. In some embodiments, the unstructured data may be captured by an abstraction process, while the structured data may be entered by the health care professional or calculated using algorithms.

Consistent with the disclosed embodiments, medical record 200 may include various documents that may be input into a generalized model, as described in further detail below. In some embodiments, the generalized model may be trained to detect one or more documents associated with representations of a biomarker or biomarker testing (or one or more particular attributes that are associated with a biomarker or testing for the biomarker attribute). For example, the generalized model may be trained to determine whether a particular document is likely to contain information associated with a biomarker or biomarker testing based on terms or phrases included in one or more documents.

Figure 2B:
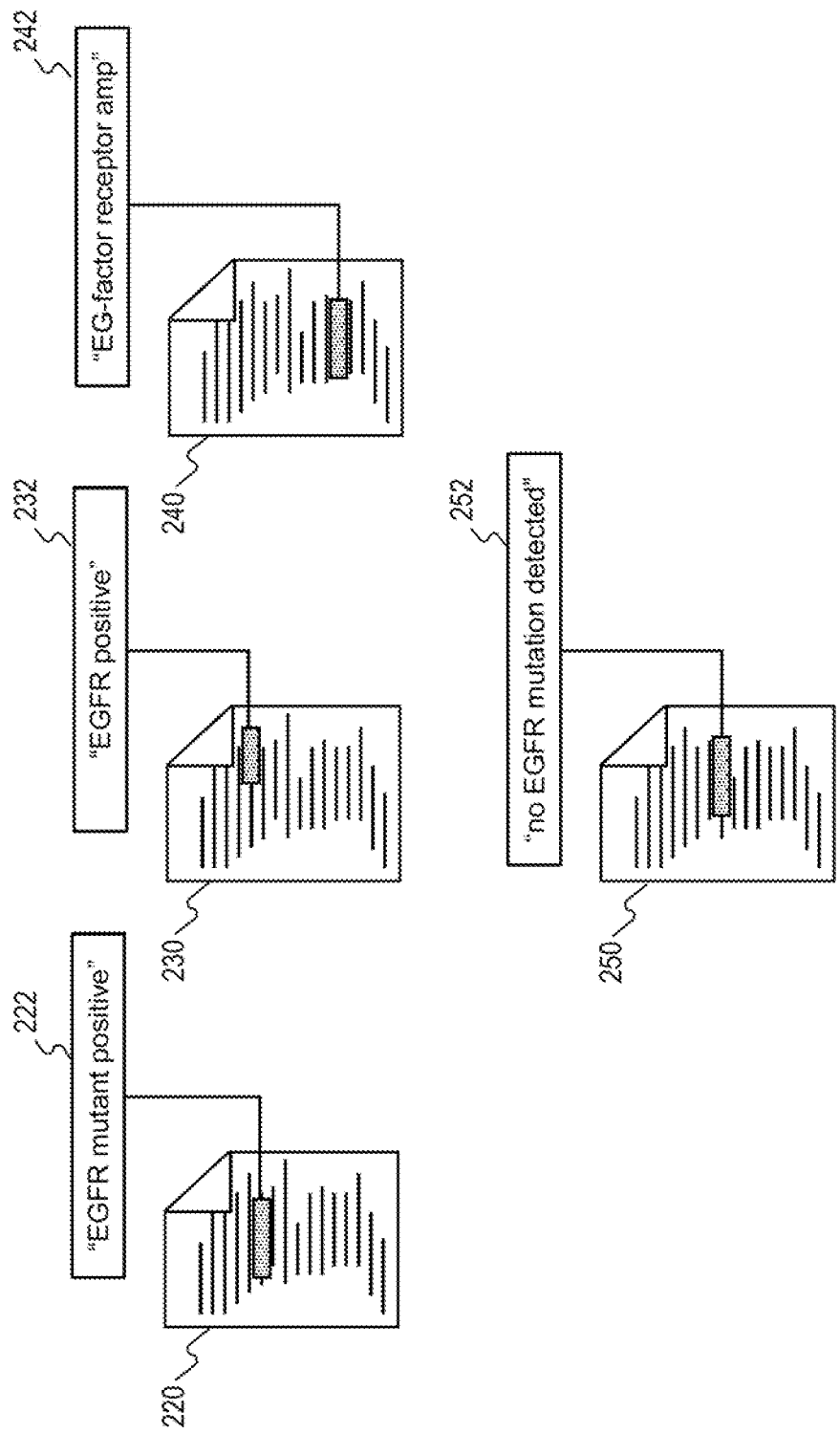
FIG. 2B is a block diagram illustrating example Phrases included in a medical record that may be evaluated, consistent with the disclosed embodiments.

FIG. 2B is a diagram illustrating example phrases included in a medical record that may be evaluated, consistent with the disclosed embodiments. As shown, one or more medical records may include documents 220, 230, 240, and 250. These documents may include structured and/or unstructured data as described above. A generalized model may be configured to identify phrases 222, 232, 242, and 252 associated with a biomarker (in this example, Estimated Glomerular Filtration Rate or "EGFR"). Phrases 222, 232, and 242 may commonly be associated with patients testing positive for a particular biomarker, whereas phrase 252 may commonly be associated with patients testing, negative for a particular biomarker. Through a model training process, a model may be configured to identify phrases that tend to indicate certain attributes associated with biomarker testing (e.g., testing positive, biomarker amplification, etc.). Accordingly, unstructured data from a medical record, such as medical record 200 may be analyzed to identify documents likely to indicate whether a patient exhibits certain attributes in association with a particular biomarker. Additional details about the generalized model and the training algorithm are provided below.

Figure 3:
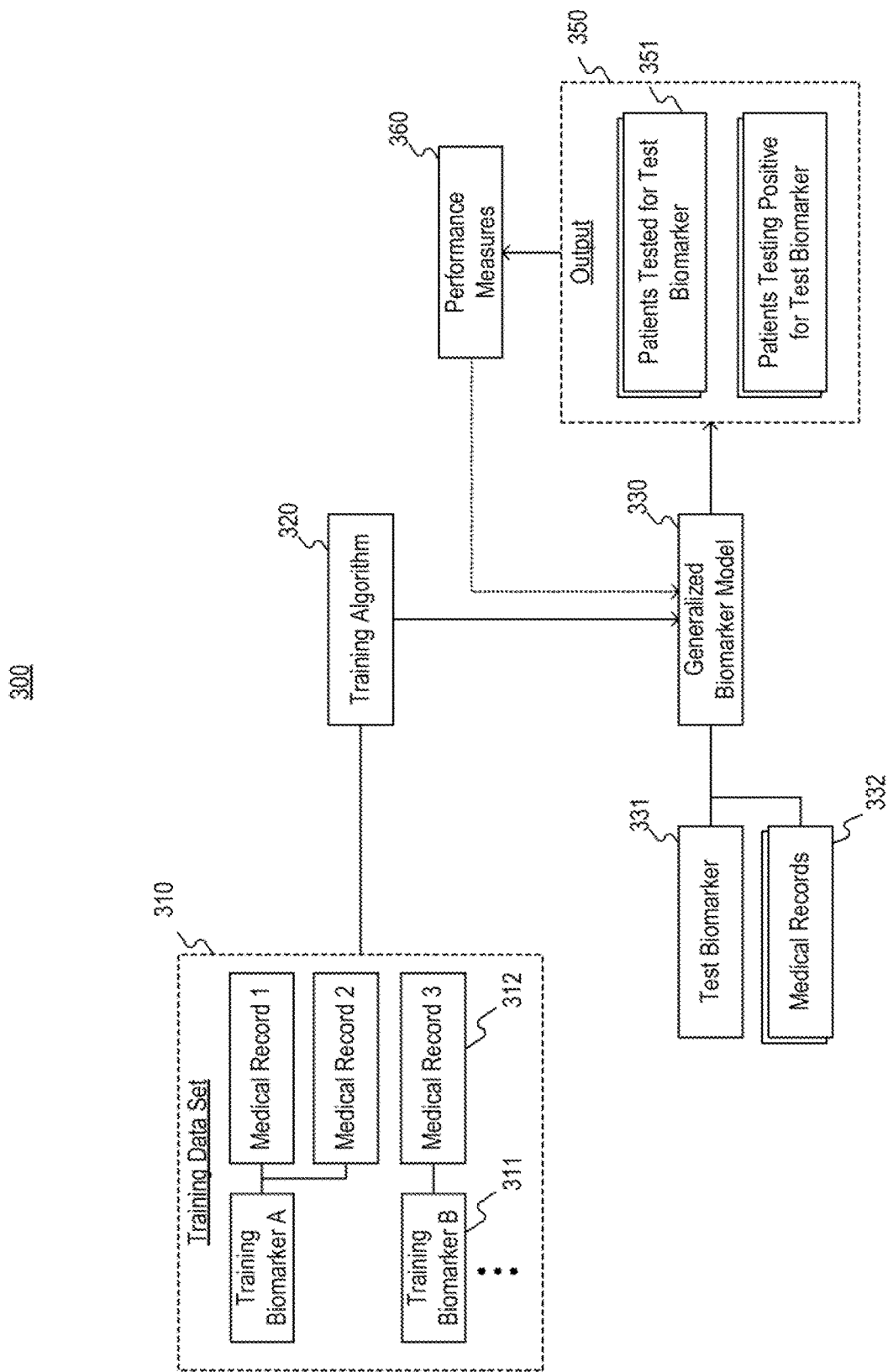
FIG. 3 is a block diagram illustrating, an exemplary machine learning process for implementing embodiments consistent with the present disclosure.

FIG. 3 illustrates an exemplary machine learning system 300 for implementing embodiments consistent with the present disclosure. Machine learning system 300 may implemented as part of system 130 (FIG. 1). For example, machine learning system 300 may be a component of or a process performed using processing engine 131. In accordance with the disclosed embodiments, machine learning system 300 may generate a generalized model (e.g., a supervised machine learning system) based on a set of training data associated with a patient and may use the model to identify patients associated with certain characteristics. For example, as shown in FIG. 3, machine learning system 300 may construct a generalized biomarker model 330 for identifying patients associated with a test biomarker 315. Machine learning system 300 may develop model 330 through a training process, for example, using training algorithm 320.

Training of model 330 may involve the use of a training data set 310, which may be input into training algorithm 320 to develop the model. Training data 310 may include a plurality of patient medical records 312 (e.g., "Medical Record 1" Medical Record 2", etc.) for which results associated with various training biomarkers 311 may already be known. For example, training biomarkers 311 may be associated with one or more medical records 312, in which the patient has been tested for training biomarkers 311. In some embodiments, each training biomarker 311 may be associated with one or more medical records 312. For example, as shown in FIG. 3, training biomarker A may be associated with more than one medical record 312 (e.g., medical record 1 and medical record 2). Training biomarkers 311 may represent biomarkers for which sufficient data is available to accurately construct generalized biomarker model 330.

In some embodiments, training data 310 may also be cleaned, conditioned and/or manipulated prior to input into training algorithm 320 to facilitate the training process. Machine learning system 300 may extract one or more features (or feature vectors) from the records and apply training algorithm 320 to determine correlations between text discussing the particular biomarker and whether the patient has been tested for the biomarker and what the test results may indicate (i.e., attributes the patient exhibits in association with the biomarker). These features may be extracted from structured and/or unstructured data as described above with respect to FIG. 2. For example, the training process may correlate words or combinations of words surrounding a biomarker identifier in the unstructured data to whether or not a patient has been tested for a biomarker, the results of the test, etc. The process for constructing generalized model 330 is described in further detail below with respect to FIG. 4A.

Once model 330 is constructed, test data, such as test biomarker 331 and medical records 332, may be input to generalized biomarker model 330. Medical records 440 may correspond to medical record 200, as described above. For example, medical records 440 may include structured and unstructured data associated with a plurality of patients, such that each patient is associated with one or more medical records. Generalized model 330 may extract features from medical records 440 to generate an output 350. Output 350 may identify patients associated medical records 332 that are also associated with test biomarker 331. For example, output 350 may identify patients that have been tested for test biomarker 311. In some embodiments, output 350 may indicate other groups of patients associated with test biomarker 311. For example, output 350 may indicate that patients have tested positive for test biomarker 331, tested negative for test biomarker 331, are diagnosed with a certain condition based on biomarker 331, prescribed a particular treatment based on test biomarker 331, etc. Each of the different groups 351 may be determined by a separate generalized biomarker model 330, or one generalized biomarker model 330 may be configured to provide multiple outputs 350 and/or patient groups 351.

In some embodiments, patients may be selected for the one or more groups based on the patient exceeding a particular likelihood threshold. For example, generalized biomarker model 330 may generate a likelihood or confidence value of each patient having been tested for the biomarker, having tested positive for the biomarker, or the like. Generalized biomarker model 330 may select patients for inclusion in one or more of groups 351 based on whether the patients exceed a particular likelihood threshold (e.g., 50%, 60%, 70%, 80%, 90%, 99%, etc.) or confidence value threshold. In some embodiments, the threshold may be adjustable based on desired levels of efficiency and performance. For example, as explained above, the model may be re-trained based on testing data (which may comprise records from the database not used to develop the model). One or more loss functions may be used to adjust the threshold.

In some embodiments, output 350 may be used to identify patients for inclusion in a cohort, as described above. For example, generalized biomarker model 330 may be used to identify patients that have been tested for test biomarker 331, that have tested positive for test biomarker 331, or the other attributes. Accordingly, further analysis may determine whether the patients are candidates for the cohort. In some embodiments, this may include verifying, based on a medical record associated with the individual, that the individual has been tested for the biomarker, or tested positive for the biomarker, etc., depending on the cohort. In some embodiments, the verification may be a manual process (e.g., performed by a trained medical professional).

In some embodiments, a remaining portion of training data 310 may be used to test the trained model 330 and evaluate its performance. For example, for each individual in the remainder of training data set 310, feature vectors may be extracted from the medical records associated with that patient. The feature vectors may be provided to model 330, and the output for that individual may be compared to the known outcome for that individual (for example, whether that individual has tested positive for a particular training biomarker 311). Deviations between the output of model 330 and the known biomarker testing for any individuals in training data set 310 may be used to generate performance measures 360, as shown in FIG. 3. Performance measures 360 may be used to update model 330 (e.g., retrain the model.) to reduce deviations between output 350 and the known patient results. For example, one or more functions of the model may be added, removed, or modified (e.g., a quadratic function may be modified into a cubic function, an exponential function may be modified into a polynomial function, or the like). Accordingly, the deviations may be used to inform decisions to modify how the features passed into model 330 are constructed or which type of model is employed. As an alternative, in some embodiments, one or more weights of the regression (or, if the model comprises a neural network, one or more weights of the nodes) may be adjusted to reduce the deviations. Where the level of deviation is within a desired limit (e.g., 10%, 5%, or less), one or more models 330 may be deemed suitable for operating on a data set for which patient results are unknown. Although described above in terms of "deviations," one or more loss functions may also be used to measure the accuracy of the model. For example, a square loss function, a hinge loss functions, a logistic loss function, a cross entropy loss function, or any other loss function may be used. In such embodiments, the updates to the model may be configured to reduce (or even minimize, at least locally) the one or more loss functions.

The accuracy of generalized biomarker model 330 may be assessed in various other ways. In some embodiments, the accuracy of generalized biomarker model 330 may be assessed based on one or more biomarker-specific models. For example, a specific biomarker model may be generated for a particular training biomarker 311. This biomarker-specific model may be developed using the techniques above, but may be trained based on medical records in which it is known whether the patient was tested for that particular biomarker. Generalized biomarker model 330 should be able to identify patients having been tested for the particular biomarker as accurately, or with similar accuracy to the biomarker-specific model. Accordingly, processing engine 131 may be configured to compare an output from the biomarker-specific model to output 350 to assess the accuracy of generalized biomarker model 330.

In other embodiments, the accuracy of generalized biomarker model 330 may be assessed based on a text search for the biomarker. For example, processing engine 131 may perform a basic text search for test biomarker 331 within the medical records and identify a group of patients that have been tested for the generalized biomarker. Generalized biomarker model 330 should outperform the basic text search as it should be able to glean additional information from the snippets. Accordingly, a comparison between the results of the text search and output 350 may be used to assess the accuracy of generalized biomarker model 330. Further, various other diagnostic queries may be performed, such as determining whether generalized biomarker model 330 has identified medical records that were not identified in the text search, which may be indicative of inaccuracies in generalized biomarker model 330.

Figure 4A:
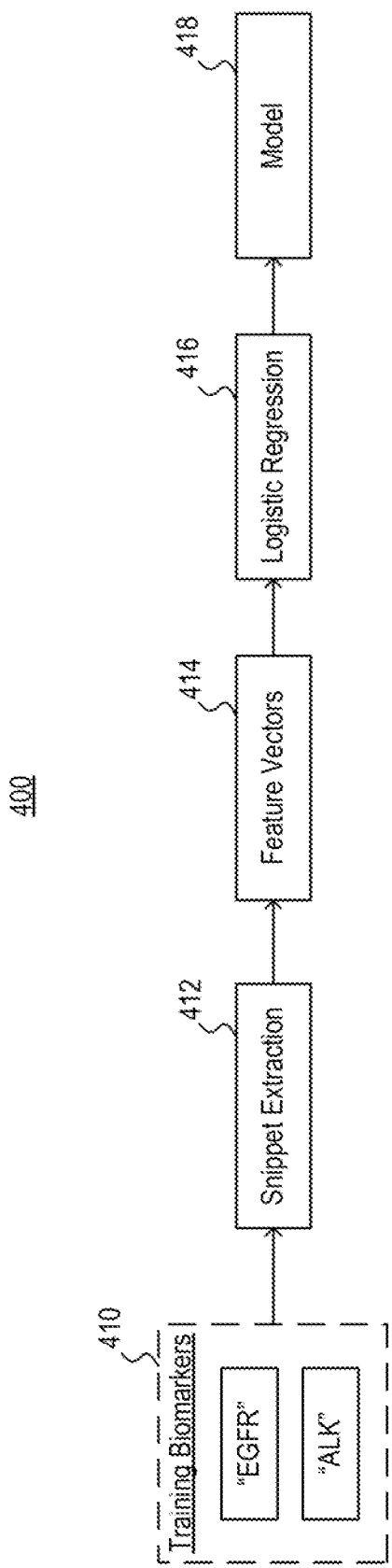
FIG. 4A is a block diagram illustrating an example process for constructing a generalized biomarker model consistent with the present disclosure.

FIG. 4A is a block diagram illustrating an example process 400 for constructing a generalized biomarker model consistent with the present disclosure. For example, process 400 may be used to construct generalized biomarker model 330 using training data set 330, as discussed above with respect to FIG. 3.

As depicted in FIG. 4A, relevant training biomarkers 410 may be selected for use in model construction. For example, training biomarkers 410 may be selected by health care professionals that are trained to perform manual, subjective determinations of whether a patient is associated with a particular biomarker. While biomarkers "EGFR" and "ALK" are provided as an example, it is understood that generalized biomarker model 330 can be constructed using any suitable biomarkers or other data. Training biomarkers 410 may represent biomarkers for which sufficient data is available to accurately construct generalized biomarker model 330. Training biomarkers 410 may correspond to training biomarkers 311, discussed above.

Training biomarkers 410 may be input to snippet extraction 412, in which text associated with biomarkers 410 is extracted from the patient medical records. While some or part of the documents of a patient's medical records may be available electronically, typed, handwritten, or printed text in the records may be converted into machine-encoded text (e.g., through optical character recognition (OCR)). The electronic text may then be searched for certain key words or phrases associated with a particular biomarker. In some embodiments, a snippet of text in a vicinity of the identified training biomarker 410 may be tested to glean additional information about the context of the word or phrase. By assessing snippets surrounding training biomarkers 410 rather than the biomarkers alone, the model may be trained to differentiate "ALK" from "ALK not tested," or the like, which may have significantly different meanings.

In some embodiments, the machine learning model can identify certain phrases in patient genetic testing reports (such as next generation sequencing) or other records, associated with the presence or non-presence of a biomarker. For example, for patients who test positive for the biomarker EGFR, their associated genetic testing records might include phrases like "positive," "mutant positive" or "amplification," and for patients who test negative for biomarker EGFR, their associated genetic testing records might include phrases like "no mutation detected."

After snippet extraction 412, feature vectorization 414 may be performed on the extracted snippets to identify a set of feature vectors. In some embodiments, structured data included in medical records from which the snippets were extracted may also be assessed with the snippets. For example, the phrases extracted, as well as any structured data considered, may be converted into a multi-dimensional vector that correlates a score to the phrases and other structured data. The score for each phrase and/or portion of structured data may represent a magnitude along a dimension associated with the corresponding phrase and/or portion. In some embodiments, the score may be binary, such that the presence of a phrase results in a magnitude of 1 along the dimension associated with the phrase while the absence of a phrase results in a magnitude of 0 along the dimension associated with the phrase. For example, the vector may have a component magnitude of 1 along the "EGER" dimension if the extracted snippets include the phrase "EGFR tested" and a component magnitude of 0 along the "EGFR" dimension if the extracted snippets only include the phrase "EGFR not tested" and not the phrase "EGFR" apart from the modifier "not." In other embodiments, the score may be non-binary and may indicate, for example, a prevalence associated with the phrase. For example, the vector may have a component magnitude of 5 along the "EGFR" dimension if the extracted snippets include five instances of the phrase "EGFR" and a component magnitude of 2 along the "ALK" dimension if the extracted snippets only two instances of the phrase "ALK." The prevalence may represent a normalized measure of instances, such as total instances per a particular number of characters, a particular number of words, a particular number of sentences, a particular number of paragraphs, a particular number of pages, or the like.

The machine learning system 300 may employ any suitable machine learning algorithms to develop model 330 based on the feature vectors. For example, training algorithm 320 may include logistic regression 416 to determine scores based on feature vectors. The scores may be correlated with or otherwise indicate whether the patient associated with the medical record has been tested for the biomarker, etc. Additionally, or alternatively, training algorithm 320 may include one or more neural networks that adjust weights of one or more nodes such that an input layer of features is run through one or more hidden layers and then through an output layer of patient results (with associated probabilities). Other types of machine learning techniques may also be used, either in combination with or separate from logistic regression 416, such as a linear regression model, a lasso regression analysis, a random forest model, a K-Nearest Neighbor (KNN) model, a K-Means model, a decision tree, a cox proportional hazards regression model, a Naïve Bayes model, a Support Vector Machines (SVM) model, or gradient boosting algorithms. The models may also be developed using an unsupervised or reinforcement machine learning process, where manual training is not required. Based on application of logistic regression 416, a resulting model may be developed in step 418. For example, generalized biomarker model 330 may be constructed based on training biomarkers 311, as described above.

Figure 4B:
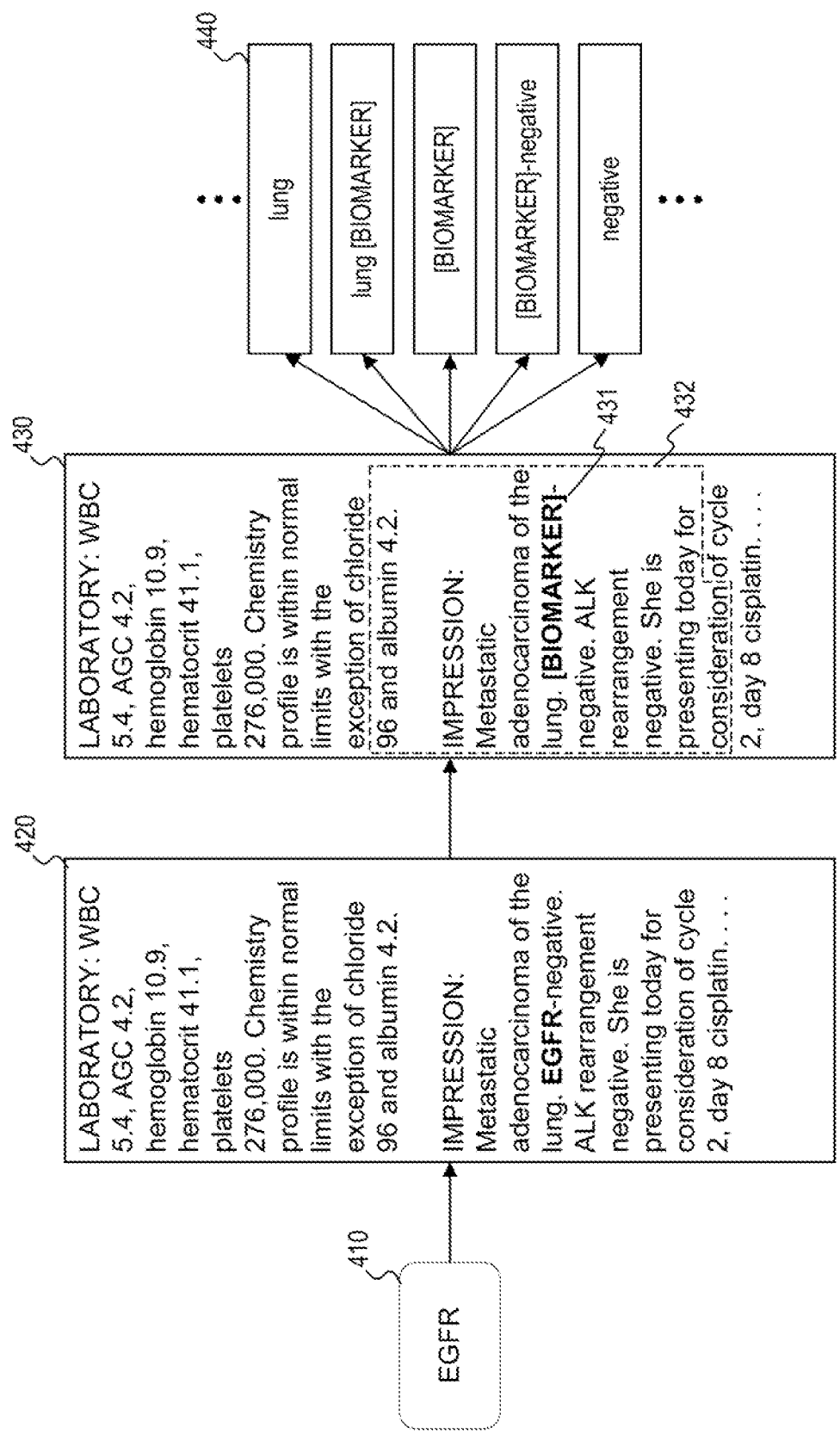
FIG. 4B is a block diagram illustrating an example technique for extracting features for constructing a generalized biomarker model consistent with the present disclosure.

FIG. 4B is a block diagram illustrating an example technique for extracting features for constructing a generalized biomarker model consistent with the present disclosure. The blocks shown in FIG. 48 may correspond to process 400.

As described above, training biomarker 410 is input into snippet extraction 412. As shown by block 420, system 130 may identify training biomarker 410 (e.g., "EGFR") from within patient medical records. In some embodiments, this may include converting typed, handwritten, or printed text in unstructured data of the patient medical records into machine-encoded text (e.g., through optical character recognition (OCR), etc.). In some embodiments, as shown in block 430, the biomarker text may be replaced by a token 431 (e.g., "[BIOMARKER]") representative of training biomarker 410 in the text. By using token 431 in place of one or more training biomarkers 410, a generalized model can be constructed based on how biomarkers are treated in the text of the medical records, rather than models based on individual biomarkers. A snippet 432 of text in a vicinity of the identified token 431 may be tested to glean additional information about the context of the word or phrase. For example, snippet 431 may be based on a predetermined number of characters or words before or after token 431, all text in the same paragraph as token 431, or various other techniques.

Based on snippet 431, a plurality of feature vectors 440 may be extracted. For example, features may be extracted based on Term-Frequency Inverse-Document-Frequency (TFIDF) vectorization, or other means. As shown in FIG. 4B, the features may be individual words, or may be bigrams (e.g., "lung [BIOMARKER]", etc.). Various other forms of features (e.g., trigram, N-gram, etc.) may also be used. System 130 may then select features and perform a logistic regression (or various other algorithms as described above) to construct generalized biomarker 330.

Figure 5:
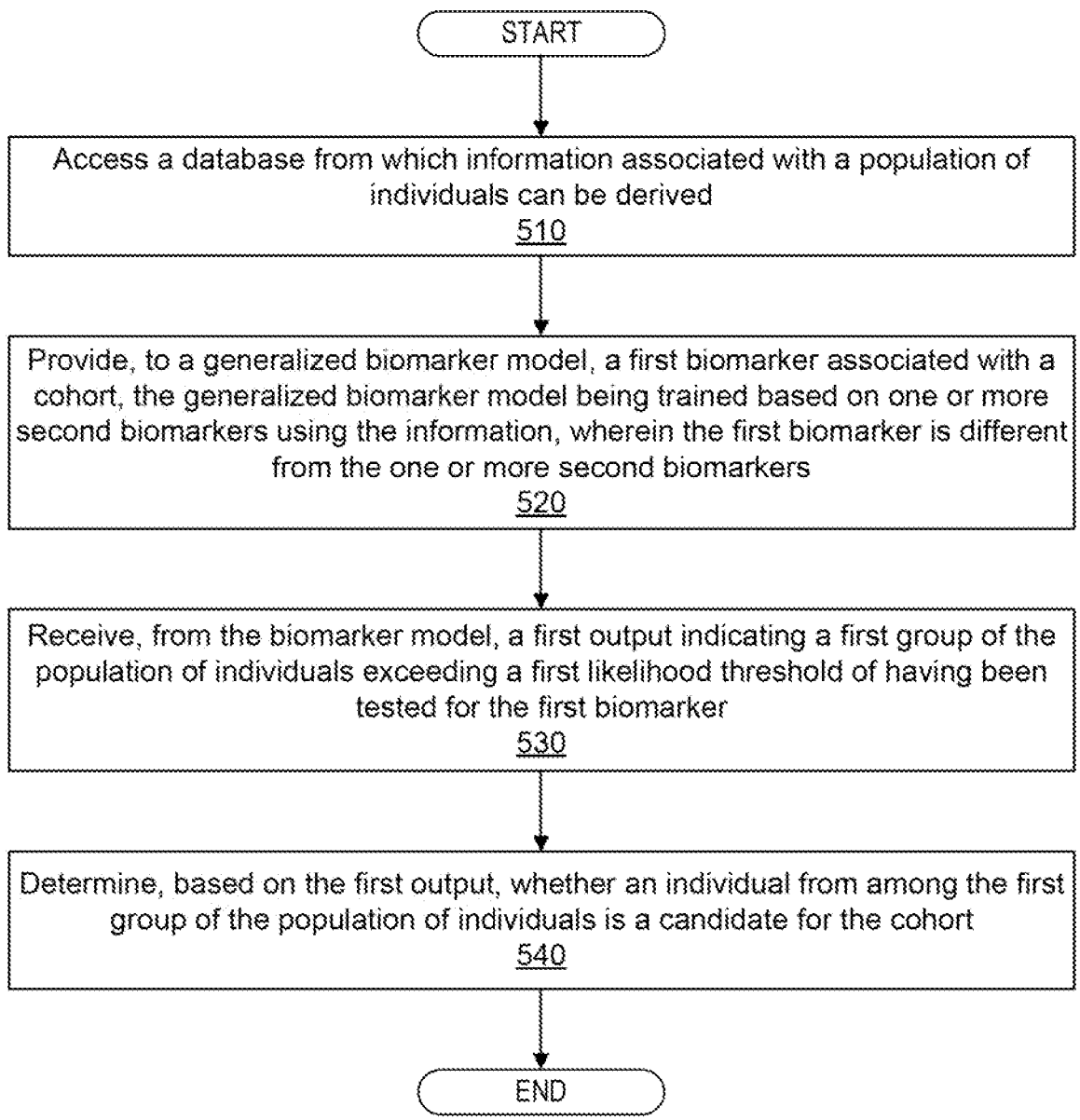
FIG. 5 is a flowchart illustrating an exemplary process for identifying candidates for a cohort based on a biomarker consistent with the present disclosure.

FIG. 5 illustrates an exemplary process 500 for identifying candidates for a cohort based on a biomarker consistent with the disclosed embodiments. Method 500 may be implemented, for example, by at least one processor of processing engine 131 of system 100, shown in FIG. 1. In some embodiments, process 500 may be performed by other devices within system 100, such as client devices 110, or other devices having access to system 130.

At step 510, method 500 may include accessing a database from which information associated with a population of individuals can be derived. In some embodiments, the information may comprise medical records associated with the population of individuals. For example, processing engine 131 may access medical records through network 140 from data sources 120 or other various sources. As described above, data sources 120 may include various sources of patient medical data including, for example, a medical provider, a laboratory, an insurance company, etc. Alternatively, or additionally, processing engine may access a local database such as database 132 to access patient medical records.

The medical record may comprise one or more electronic files, such as text files, image files, PDF files, XLM files, YAML files, or the like. In some embodiments, the medical records (e.g., medical record 200) may include structured information (e.g., structured data 212) and unstructured information (e.g., unstructured data 211) associated with the population of individuals, as described above. For example, the structured information may include a gender, a birth date, a race, a weight, a lab result, a vital sign, a diagnosis date, a visit date, a medication order, a diagnosis code, a procedure code, a drug code, a prior therapy, or a medication administration. The unstructured information may include text written by a health care provider, a radiology report, a pathology report, or various other forms of text associated with the patient. In some embodiments, at least a portion of the unstructured information has been subject to an optical character recognition process, as discussed above. Each medical record may be associated with a particular patient and, in some embodiments, multiple medical records may be associated with a particular patient. The medical record may not be limited to data from medical institutions and may include other related forms of data, such as claims data (e.g., from an insurance company), patient-reported data, or other information associated with the patient's treatment or well-being.

At step 520, method 500 may include providing, to a generalized biomarker model, a first biomarker associated with a cohort, the generalized biomarker model being trained based on one or more second biomarkers using the information, wherein the first biomarker is different from the one or more second biomarkers. For example, the one or more second biomarkers may correspond to training biomarkers 311 and the first biomarker may correspond to test biomarker 331, as discussed above with respect to FIG. 3. Accordingly, the one or more second biomarkers may be used to construct generalized biomarker model 330. In some embodiments, the one or more second biomarkers may represent biomarkers for which sufficient data is available for constructing generalized biomarker model 330. For example, the one or more second biomarkers may appear in the information more than the first biomarker. In some embodiments, the generalized biomarker model may be trained based on the unstructured information, as discussed above. In some embodiments, the generalized biomarker model may be developed at least in part based on feature vectors extracted from the information based on the one or more second biomarkers. For example, generalized biomarker model 330 may be developed based on feature vectors 440 as described in FIG. 4B. Further, in some embodiments, the feature vectors may comprise at least one biomarker token (e.g., token 431) representing text associated with the at least one second biomarker.

Step 520 may include additional sub-steps to facilitate analysis of the medical record, such as conditioning or altering information in the record. Processing engine 131 may employ various techniques to interpret the structured or unstructured information. For example, typed, handwritten, or printed text in the medical records may be converted into machine-encoded text (e.g., through optical character recognition (OCR)).

At step 530, method 500 may include receiving, from the biomarker model, a first output indicating a first group of the population of individuals exceeding a first likelihood threshold of having been tested for the first biomarker. For example, generalized biomarker model 330 may generate output 350 which may comprise a group 351 indicating patients having been tested for the first biomarker. In some embodiments, the likelihood threshold is adjustable based on levels of efficiency and performance of the model. In some embodiments, the biomarker model may generate the first output using a binary classification algorithm. For example, the binary classification algorithm may include at least one of a logistic regression, a random forest, gradient boosted trees, support vector machines, or neural networks. In some embodiments the classification algorithm may include various other algorithms as described above (e.g., a cox proportional hazards regression, a lasso regression analysis network, etc.). In some embodiments, step 530 may include further steps, such as storing the first output for access by a user of the generalized biomarker model. In some embodiments, step 530 may comprise transmitting the first output to one or more users or devices. For example, system 120 may transmit the first output to client devices 100 over network 140.

In some embodiments, process 500 may further include receiving, from the generalized biomarker model, a second output indicating a second group of the population of individuals exceeding a second likelihood threshold of having been tested positive for the first biomarker, the individual being included in the second group. In some embodiments, the second group of patients may be identified in the first output, along with the first group of patients. For example, the generalized biomarker model may be configured to determine both a first group of patients having been tested for the biomarker and a second group of patients having tested positive for the biomarker. In other embodiments, a separate generalized biomarker model may be used for identifying the second group of patients.

At step 540, method 500 may include determining, based on the first output, whether an individual from among the first group of the population of individuals is a candidate for the cohort. For example, determining whether the individual is a candidate for the cohort may comprise verifying, based on a medical record associated with the individual, that the individual has been tested for the biomarker. As discussed above, this may be a manual process (e.g., by a trained medical professional) to determine whether the individual was actually tested for the first biomarker. In embodiments, where the generalized biomarker model is configured to determine whether the patient is associated with a particular result of the test (e.g., the patient having tested positive for the first biomarker), determining whether the individual is a candidate for the cohort may comprise verifying, based on a medical record associated with the individual, that the individual has tested positive for the biomarker.

In some embodiments, process 500 may further include additional steps. For example, process 500 may be configured to verify the accuracy of the generalized biomarker model. In some embodiments, the accuracy of the generalized biomarker model may be assessed based on a biomarker model specific to the first biomarker. Accordingly, process 500 may comprise providing the first biomarker to a biomarker specific model, the biomarker specific model being trained based on the first biomarker using the medical records. Process 500 may further comprise receiving, from the biomarker specific model, a third output indicating a third group of the population of individuals exceeding a likelihood threshold of having been tested for the at least one biomarker. Further, process 500 may include verifying the accuracy of the generalized biomarker model by comparing the first output to the third output. For example, differences between results from the generalized biomarker model and the biomarker specific model may indicate whether the generalized biomarker model is effective for identifying patients having been tested for a variety of different biomarkers.

In other embodiments, the accuracy of the generalized biomarker model may be verified by comparing the results to a search function. Accordingly, process 500 may comprise searching the medical records for the first biomarker to generate a fourth output indicating a fourth group of the population of individuals having been tested for the at least one biomarker. For example, system 130 may search for words associated with the first biomarker within the medical records using a plain text search function. Process 500 may further comprise verifying the accuracy of the generalized biomarker model by comparing the first output to the fourth output. Ideally, the generalized biomarker model will perform better for identifying patients for inclusion in a cohort than a basic text search for the first biomarker. Various other means for testing the accuracy of the generalized biomarker may also be used. Further, process 500 may include additional steps, such as updating the generalized biomarker model based on the determined accuracy, etc.

In some embodiments, process 500 may be applied to other characteristics besides biomarkers. Accordingly, in some embodiments, process 500 may comprise accessing a database from which information associated with a population of individuals can be derived (step 520); providing, to a generalized model, a first characteristic associated with a cohort, the generalized model being trained based on one or more second characteristics using the information, wherein the first characteristic is different from the one or more second characteristics (step 540); receiving, from the generalized model, a first output indicating a first group of the population of individuals exceeding a first likelihood threshold of been associated with the first characteristic (step 560); and determining, based on the first output, whether an individual from among the first group of the population of individuals is a candidate for the cohort (step 580). In some embodiments, the characteristic may apply to biomarkers, as discussed above. Accordingly, the first characteristic may comprise a first biomarker; the one or more second characteristics may comprise one or more second biomarkers, and the first output may be indicative of the first group of individuals having been tested for the first biomarker. In other embodiments, the first characteristic may comprise a first drug; the one or more second characteristics may comprise one or more second drugs; and the first output may be indicative of the first group of individuals having been treated using the first drug.

Identifying Patients Using a Generalized Biomarker Model

As described above, a generalized biomarker model may be used to identify patients for inclusion in a cohort. In particular, the generalized biomarker model may be trained to identify patients having a likelihood of exhibiting a certain trait or characteristic based on medical records associated with the patients. In some embodiments, this may include identifying patients having a likelihood of having been tested for a particular biomarker, a likelihood of having tested positive for a particular biomarker, or similar characteristics associated with biomarkers. The generalized biomarker model may further output confidence scores, or other indicators of a likelihood of each patient exhibiting the selected trait or characteristic. Accordingly, a group of patients exhibiting a particular trait may be selected based on his or her associated confidence score, which may be compared to a likelihood threshold. Identified patients with confidence scores exceeding the likelihood threshold may then be surfaced as potential candidates for inclusion in a cohort. For example, the group of patients may be identified to a trial coordinator, who may review medical records for each patient for suitability for inclusion in a patient trial. Selected patients may then be identified to a medical practice (e.g., a healthcare facility) for treatment, including in a clinical trial, or the like.

In some embodiments, the likelihood threshold may be defined to accurately identify patients. For example, the likelihood threshold may be tuned to be as inclusive as possible while minimizing a number of false positive identifications of patients as testing positive for a particular biomarker. Surfacing patients based on a confidence of exhibiting a particular trait alone may present issues associated with treatment of patients, developing clinical trials, or other goals associated with identifying patients. In some cases, a medical practice may be overwhelmed if too many patients are surfaced as a result of the generalized biomarker model. For example, each practice may have a limited total number of patients that it can accept based on current staff, facilities, supplies, etc. Further, trial or research coordinators may need to review medical records for each identified patient to determine eligibility for inclusion in a clinical trial. For example, a trial coordinator may typically review 4-10 patients per day. Accordingly, surfacing too many patients within a short time may overwhelm medical practices and/or trial coordinators. Further, surfacing patients based on a confidence of exhibiting a particular biomarker alone may result in underrepresentation of patients with certain biomarkers. For example, the model may surface large amounts of patients exhibiting more commonly tested for biomarkers. However, the model may surface relatively low numbers of patients associated with less common biomarkers that may still be relevant to practices.

To address these and other technical problems associated with identifying patients, the disclosed systems may determine likelihood thresholds for selections of patients based on a number of patients to be surfaced. For example, the disclosed systems and methods may adjust one or more likelihood thresholds to avoid overwhelming trial coordinators or practices. In some embodiments, the likelihood thresholds may be adjusted at a biomarker level, rather than at a practice level. For example, the disclosed system may be configured to apply the generalized biomarker model to multiple biomarkers and surface a group of patients associated with each biomarker model to the practice. The disclosed systems may adjust the likelihood threshold for each biomarker individually. Accordingly, the number of patients that are surfaced to the practice may be adjusted for each biomarker being considered.

As discussed above, a generalized biomarker model may output confidence scores indicating a degree of certainty that a patient is associated with a particular trait (e.g., having been tested for a biomarker, testing positive for a particular biomarker, etc.). The likelihood threshold may be adjusted such that only patients with confidence scores exceeding a value set by the likelihood threshold are surfaced by the system. For example, a likelihood threshold set at 95% for a particular biomarker may result in patients with confidence scores greater than 95% being surfaced. Thus, a lower likelihood threshold may be more inclusive and may result in more patients being surfaced. In some embodiments, these thresholds may be set manually by users. For example, medical practices or system administrators may adjust one or more thresholds through a user interface. The thresholds may be adjusted directly, for example, by adjusting a likelihood threshold value, or indirectly, for example, by setting a patient number limit, providing feedback that a practice is receiving too many patients, etc. In some embodiments, the thresholds may be adjusted automatically.

Various factors may be considered when determining the likelihood threshold for each biomarker. In some embodiments, a rarity or relative prevalence of the biomarker being exhibited in patients compared to other biomarkers may be used to determine a likelihood threshold for each biomarker. For example, a particular biomarker such as neorotrophic tropomyosin receptor kinase ("NTRK") may be relatively rare and may only be tested for (or tested positive for) in a relatively small number of patients, but may still be important to practices. Accordingly, the likelihood threshold associated with the NTRK biomarker may be set lower (e.g., more inclusive of patients) as compared to other biomarkers. For example, there may be less concern about overwhelming a practice with patients exhibiting the NTRK biomarker traits because of the relative rarity associated with the biomarker. Conversely, for more commonly tested or exhibited biomarkers, such as the human epidermal growth factor receptor 2 ("HER2"), the threshold may be set higher to avoid overwhelming the practice.

In some embodiments, the likelihood threshold for a particular biomarker may be determined based on an actionability associated with the biomarker. In other words, a likelihood threshold may be determined based on how readily patients associated with the particular biomarker may be treated by a practice. For example, if a particular biomarker is associated with a long or complicated treatment process, the likelihood threshold may be increased to reduce the number of patients associated with the biomarker that are presented to the practice. Conversely, biomarkers associated with relatively short treatment times may be lowered to increase the number of patients.

Various other factors may also be considered when adjusting the likelihood thresholds. In some embodiments, the likelihood thresholds may consider more long-term factors associated with a clinical trial. For example, a particular trial may have a predefined number of patients associated with a particular biomarker to fill or close the trial. If the number of patients identified by the model indicates the trial group is likely to be filled over the course of the study, the threshold may be increased. Conversely, if it appears the trial may not be filled over the course of the study, the threshold may be decreased to include more patients. This may be assessed or adjusted periodically throughout the trial.

In some embodiments, the likelihood threshold may be informed based on a predetermined cohort size (e.g., based on capacity of a practice) in addition to determined likelihood values for the patients. For example, if a practice has a capacity of 30 patients, a predetermined cohort size may be set at 30 to limit the number of individuals that are surfaced. The system may compare determined likelihoods for individuals to a likelihood threshold, which as described above may reflect a confidence in an individual having (or having been tested for) an attribute associated with a biomarker. If only 20 individuals meet the minimum level of confidence set by the likelihood threshold, only those 20 patients will be surfaced, even though the practice's capacity is greater. Conversely, if the practice has a capacity for 20 patients, and 40 patients satisfy a likelihood threshold of having a particular biomarker attribute only 20 of the individuals will be surfaced. In this situation, the likelihood scores of the patients may be used to select patients to be surfaced. For example, the patients having likelihood scores showing the most confidence that the individuals have the attribute (or have been tested for the attribute) may be surfaced.

FIG. 6 illustrates an example user interface 600 for selecting patients for a clinical trial, consistent with the disclosed embodiments. User interface 600 may include various controls and/or options for specifying patients to be surfaced for a particular clinical trial. For example, an administrator may use user interface 600 to surface patients with particular diseases for a trial, particular metastatic statuses, particular lines of therapy, or the like. As shown in FIG. 6, user interface 600 may include a field 610 for entering or specifying a name of a cohort. User interface may include various other controls, such as controls 620, 630, 640, and 650. Control 620 may be used to toggle a patient matching status of a particular cohort. For example, this ma determine whether patients are actively matched for a particular cohort based on various inclusion criteria. Control 630 may allow a user to input criteria associated with a particular disease or diseases. Control 630 may also allow for a user to specify that no diseases are to be included as a criteria for the trial. Control 640 may allow a user to specify a metastatic status as part of the inclusion criteria. Similarly, control 650 may allow a user to specify a particular line of therapy (or lines of therapy) as part of the inclusion criteria. In some embodiments, user interface 600 may further include options for limiting a number of patients to be surfaced. For example, user interface 600 may include additional controls for setting a maximum number of patients, or for adjusting individual likelihood thresholds. While the various controls shown in FIG. 6 are provided by way of example, one skilled in the art would recognize various other controls that may be included for specifying inclusion criteria for a particular trial.

Figure 7:
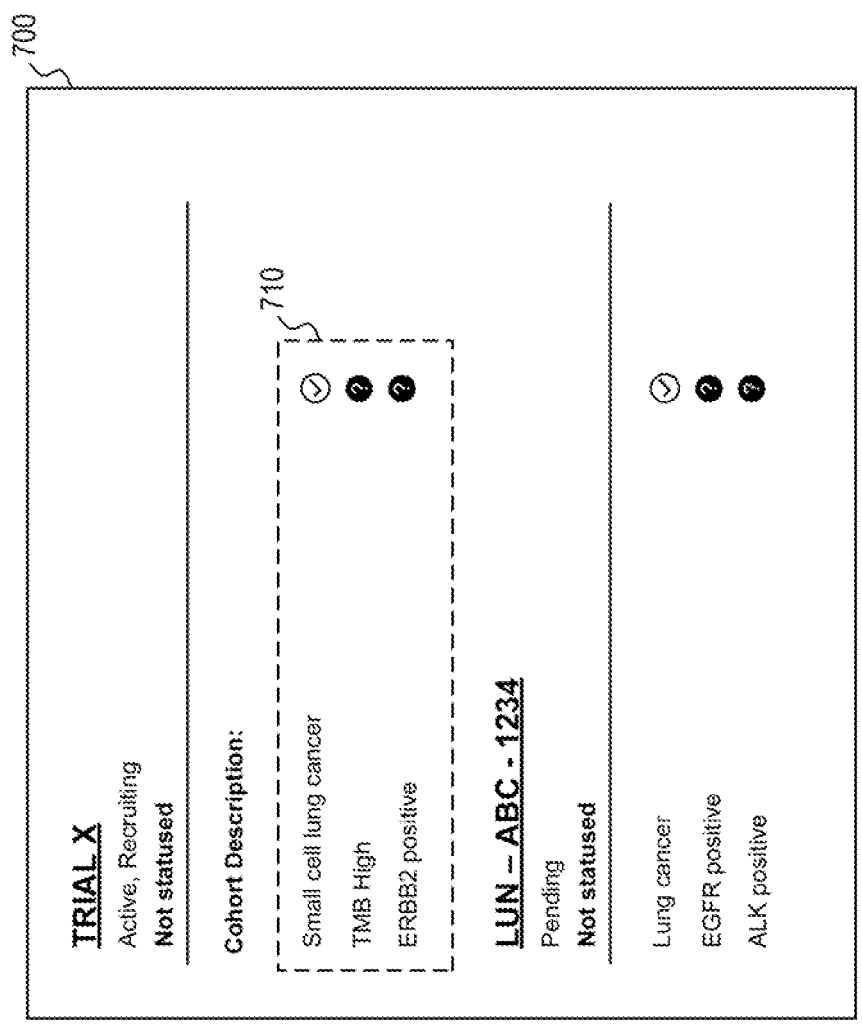
FIG. 7 illustrates an example display showing status information for various clinical trials, consistent with the disclosed embodiments.

The disclosed systems may further allow a user, such as an administrator, to view status information for various clinical trials. FIG. 7 illustrates an example display 700 showing status information for various clinical trials, consistent with the disclosed embodiments. For example, a Trial X may be active and currently recruiting patients. Display 700 may further indicate particular diseases, biomarker testing and/or test results, or other traits or attributes associated with each clinical trial, as shown in frame 710.

Based on these biomarker-specific likelihood thresholds the number of patients surfaced for each biomarker, as well as the total number of patients for each practice may be closely monitored and adjusted. Accordingly, the disclosed systems and methods may allow for generating tailored sets of patient groups based on practice and trial coordinator capacity, while at the same time maintaining high accuracy in the selection of patients to be surfaced.

In some embodiments, the disclosed systems and methods may include tuning or adjusting the generalized biomarker model based on training data that is used for particular trials. For example, some clinical trials may have predetermined sets of patients or patient data that is associated with the trial. An administrator or other user of the generalized biomarker may have limited control over the data available to the model. Accordingly, the generalized model may be adjusted or tuned based on the available data. For example, this may include comparing the trial-specific data with a set of data used to train the generalized biomarker. Based on this comparison, the model may be tuned to account for differences between the trial-specific data set and the training data. This may include adjusting the model based on patient demographic information, patient treatment information, types of biomarkers being tested for, a number of patients included in the trial-specific data, or various other factors.

Figure 8:
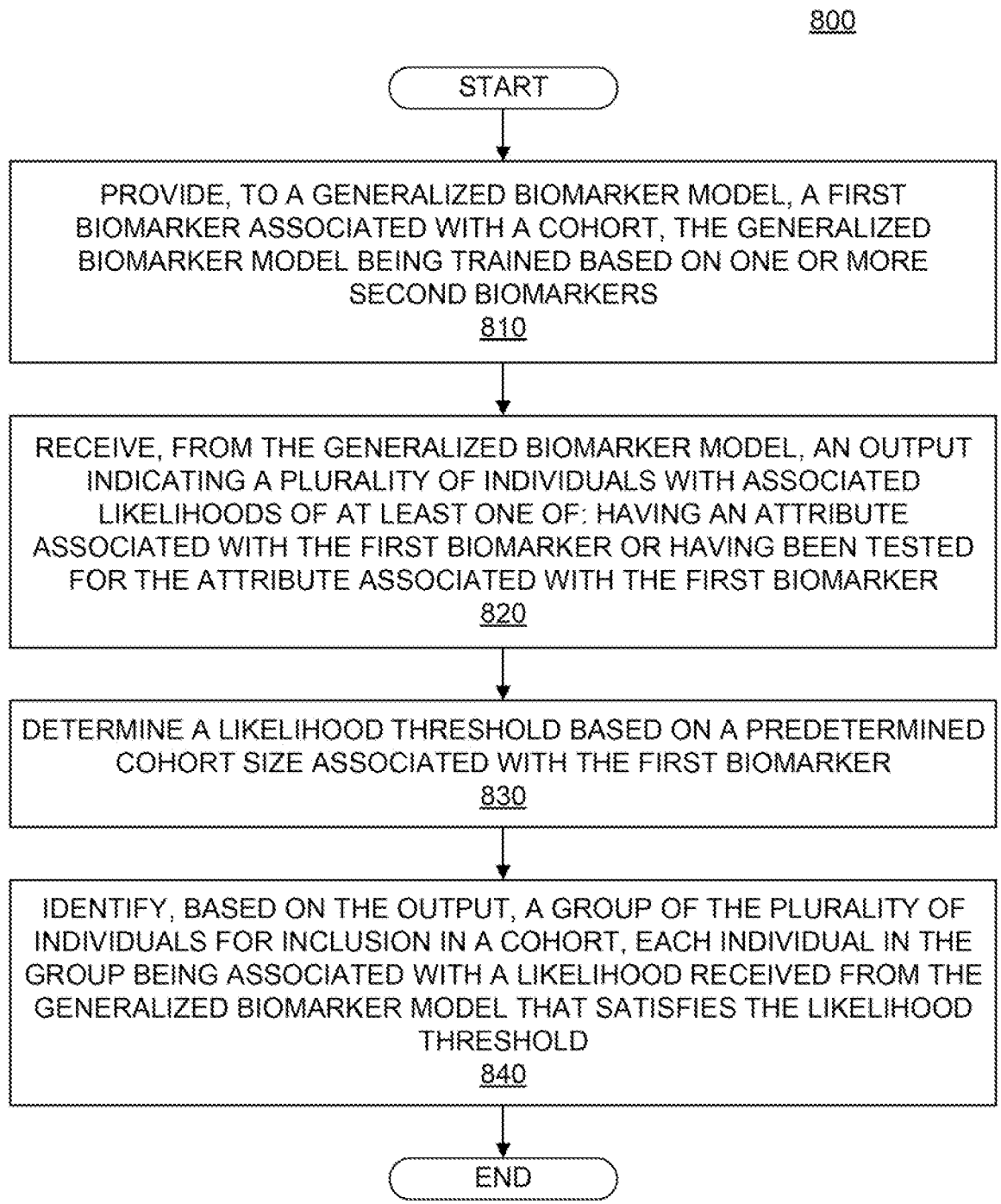
FIG. 8 illustrates an exemplary process fear identifying a group of patients for a cohort using a generalized biomarker model, consistent with the disclosed embodiments.

FIG. 8 illustrates an exemplary process 800 for identifying a group of patients for a cohort using a generalized biomarker model, consistent with the disclosed embodiments. Method 800 may be implemented, for example, by at least one processor of processing engine 131 of system 100, shown in FIG. 1. In some embodiments, process 800 may be performed by other devices within system 100, such as client devices 110, or other devices having access to system 130. In some embodiments, process 800 may include various other steps not shown in FIG. 8, including those described above with respect to FIG. 5.

At step 810, process 800 may include providing, to a generalized biomarker model, a first biomarker associated with a cohort. The generalized biomarker model may be trained based on one or more second biomarkers to detect documents associated with representations of a biomarker or biomarker testing (or one or more particular attributes that are associated with a biomarker or biomarker testing), as described above. Consistent with the embodiments of the present disclosure, the first biomarker may be different from the one or more second biomarkers. For example, the one or more second biomarkers may correspond to training biomarkers 311 and the first biomarker may correspond to test biomarker 331, as discussed above with respect to FIG. 3. Accordingly, the one or more second biomarkers may be used to construct generalized biomarker model 330. In some embodiments, the one or more second biomarkers may represent biomarkers for which sufficient data is available for constructing generalized biomarker model 330. For example, the one or more second biomarkers may appear in the information more than the first biomarker. The generalized biomarker model may be trained based on the unstructured information, as discussed above.

In some embodiments, process 800 may further include training the generalized biomarker model based on the one or more second biomarkers. As described in further detail above with respect to FIGS. 4A and 4B, this may include identifying representations of the one or more second biomarkers in a plurality of training medical records, extracting snippets of text surrounding the representations of the one or more second biomarkers, generating a plurality of feature vectors based on the snippets, and training the generalized biomarker model to detect documents (which may also include attributes) associated with the one or more second biomarkers based on the plurality of feature vectors. For example, training the generalized biomarker model to detect documents associated with the one or more second biomarkers may include applying a logistic regression algorithm, as described above. Further, in some embodiments, the feature vectors may comprise at least one biomarker token (e.g., token 431) representing text associated with the at least one second biomarker.

In some embodiments, step 810 may include additional sub-steps to facilitate analysis of the medical record, such as conditioning or altering information in the record. Processing engine 131 may employ various techniques to interpret the structured or unstructured information. For example, typed, handwritten, or printed text in the medical records may be converted into machine-encoded text (e.g., through optical character recognition (OCR)), or the like.

At step 820, process 800 may include receiving, from the generalized biomarker model, an output indicating a plurality of individuals with associated likelihoods of at least one of: having an attribute associated with the first biomarker or having been tested for the attribute associated with the first biomarker. For example, generalized biomarker model 310 may generate output 380 which may comprise a group 381 indicating patients exhibiting one or more particular attributes associated with a biomarker (e.g., having tested positive, exhibiting an amplification associated with a biomarker, or the like). In some embodiments, the generalized biomarker may access information about a plurality of individuals, which may be analyzed to generate the output. For example, process 800 may include accessing a database from which information associated with a population of individuals can be derived. In some embodiments, the information may comprise medical records associated with the population of individuals. For example, processing engine 131 may access medical records through network 140 from data sources 120 or other various sources. As described above, data sources 120 may include various sources of patient medical data including, for example, a medical provider, a laboratory, an insurance company, etc. Alternatively, or additionally, processing engine may access a local database such as database 132 to access patient medical records. The generalized biomarker may be configured to generate the output based on analyzing the information in association with the first biomarker.

At step 830, process 800 may include determining a likelihood threshold based on a predetermined cohort size associated with the first biomarker. For example, a practice may have a limited total number of patients that it can accept based on current staff, facilities, supplies, etc. Accordingly, the predetermined cohort size may be based on a total capacity of a healthcare provider. Alternatively or additionally, the predetermined cohort size may be defined as a separate value from the capacity of a healthcare facility. Accordingly, the likelihood threshold may be determined based on the predetermined cohort size associated with the first biomarker in addition to or separate from a total capacity for a healthcare facility. In some embodiments, the likelihood threshold may be based on a combination of multiple factors. For example, the likelihood threshold may be based on a threshold confidence level (determined based on the likelihoods associated with the plurality of patients determined using the model) in conjunction with a predetermined cohort size, as described above. In other words, the likelihood threshold may be configured such that individuals exceeding a particular likelihood are surfaced up to a predetermined cohort size.

The likelihood threshold may be adjusted such that the number of patients selected for inclusion meet the predetermined cohort size. Various other factors may be used for determining the likelihood threshold. In some embodiments, the likelihood threshold may further be determined based on a relative prevalence of the first biomarker. For example, a particular biomarker may be relatively rare and may only be tested for (or tested positive for) in a relatively small number of patients. Accordingly, the likelihood threshold associated with rare biomarkers may be set lower (i.e., more inclusive of patients) as compared to other biomarkers, as there would be less concern for receiving too many patients associated with this particular biomarker.

As another example, the likelihood threshold may be determined based on a relative ability of a healthcare provider to perform an action based on the first biomarker. These actions may include any actions a healthcare provider may take in association with a cohort. This may include patient intake, additional testing of the patient, treatment of the patient, diagnosis of the patient, or the like. The ability of a healthcare provider to perform the action may be based on various attributes of the healthcare provider, such as staffing, size, equipment, scheduling considerations, or other resources or conditions of the healthcare provider. In some embodiments, the ability to perform an action may be based on attributes of the action. For example, longer or more complicated actions (e.g., treatments, etc.) may place a higher demand on a healthcare provider than shorter or less complicated actions.

As another example, the likelihood threshold is further determined based on a likelihood the cohort will be filled over the course of a particular study. This may depend on a number of patients identified by the generalized model. For example, if the number of patients identified by the model indicates the trial group is likely to be filled over the course of the study, the threshold may be increased. Conversely, if it appears the trial may not be filled over the course of the study, the threshold may be decreased to include more patients. Accordingly, the likelihood threshold may be adjusted dynamically throughout an ongoing trial.

In step 840, process 800 may include identifying, based on the output, a group of the plurality of individuals for inclusion in a cohort. Each individual in the group of the plurality of individuals may be associated with a likelihood received from the generalized biomarker model that satisfies the likelihood threshold. In some embodiments, process 800 may include further steps to verify whether an individual should be considered a candidate, For example, determining whether the individual is a candidate for the cohort may comprise verifying, based on a medical record associated with the individual, that the individual has been tested for the attribute associated with the first biomarker.

As described above, the generalized biomarker model may be trained such that it may be used in association with a variety of biomarkers, and not only the biomarkers it was trained with (i.e., the second biomarkers). Accordingly, process 800 may further include providing, to the generalized biomarker model, a third biomarker; receiving, from the generalized biomarker model, an additional output indicating an additional plurality of individuals with associated likelihoods of at least one of: having an additional attribute associated with the third biomarker or having been tested for the additional attribute associated with the third biomarker, determining a third biomarker likelihood threshold based on a predetermined cohort size associated with the third biomarker for inclusion in the cohort; and identifying, based on the additional output, an additional group of the additional plurality of individuals for inclusion in the cohort, each individual in the additional group of the additional plurality of individuals being associated with a likelihood received from the generalized biomarker model that satisfies the third biomarker likelihood threshold. In other words, process 800 may be repeated with another biomarker using the same generalized biomarker model.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A model-assisted system, the system comprising:
    at least one processor programmed to:
        access a database from which information associated with a plurality of individuals can be derived, wherein the information includes a plurality of patient medical records associated with the plurality of individuals;
        provide, to a generalized biomarker model, a first biomarker associated with a cohort, the generalized biomarker model being trained based on one or more second biomarkers to detect one or more documents associated with representations of the first biomarker or biomarker testing, wherein the first biomarker is different from the one or more second biomarkers;
        receive, from the generalized biomarker model, an output indicating likelihoods, associated with the plurality of individuals, of at least one of: having an attribute associated with the first biomarker or having been tested for the attribute associated with the first biomarker;
        determine a likelihood threshold based on a predetermined cohort size associated with the first biomarker; and
        identify, based on the output, a group of the plurality of individuals for inclusion in the cohort, each individual in the group of the plurality of individuals being associated with a likelihood received from the generalized biomarker model that satisfies the likelihood threshold.

2. The model-assisted system of claim 1, wherein the likelihood threshold is further determined based on a relative prevalence of the first biomarker.

3. The model-assisted system of claim 1, wherein the likelihood threshold is further determined based on a likelihood the cohort will be filled over the course of a particular study.

4. The model-assisted system of claim 1, wherein the predetermined cohort size is based on a total capacity of a healthcare provider.

5. The model assisted system of claim 1, wherein at least one processor is further programmed to:
    provide, to the generalized biomarker model, a third biomarker;
    receive, from the generalized biomarker model, an additional output indicating an additional plurality of individuals with associated likelihoods of at least one of: having an additional attribute associated with the third biomarker or having been tested for the additional attribute associated with the third biomarker;
    determine a third biomarker likelihood threshold based on a predetermined cohort size associated with the third biomarker; and
    identify, based on the additional output, an additional group of the additional plurality of individuals for inclusion in the cohort, each individual in the additional group, of the additional plurality of individuals being associated with a likelihood received from the generalized biomarker model that satisfies the third biomarker likelihood threshold.

6. The model-assisted system of claim 1, wherein the likelihood threshold is further determined based on the predetermined cohort size associated with the first biomarker and a total capacity for a healthcare facility.

7. The model-assisted system of claim 1, wherein the at least one processor is further programmed to train the generalized biomarker model based on the one or more second biomarkers.

8. The model-assisted system of claim 7, wherein training the generalized biomarker includes:
    identifying representations of the one or more second biomarkers in a plurality of training medical records;
    extracting snippets of text surrounding the representations of the one or more second biomarkers;
    generating a plurality of feature vectors based on the snippets; and
    training the generalized biomarker model to detect documents associated with the one or more second biomarkers based on the plurality of feature vectors.

9. The model-assisted system of claim 7, wherein training the generalized biomarker model to detect documents associated with the one or more second biomarkers includes applying a logistic regression algorithm.

10. A model-assisted system, the system comprising:
    at least one processor programmed to:
        provide, to a generalized biomarker model, a first biomarker associated with a cohort, the generalized biomarker model being trained based on one or more second biomarkers to detect one or more documents associated with representations of the first biomarker or biomarker testing, wherein the first biomarker is different from the one or more second biomarkers;
        receive, from the generalized biomarker model, an output indicating a plurality of individuals with associated likelihoods of at least one of: having an attribute associated with the first biomarker or having been tested for the attribute associated with the first biomarker;
        determine a likelihood threshold based on a predetermined cohort size associated with the first biomarker, a relative prevalence of the biomarker, and a relative ability of a healthcare provider to perform an action based on the first biomarker; and
        identify, based on the output, a group of the plurality of individuals for inclusion in the cohort, each individual in the group of the plurality of individuals being associated with a likelihood received from the generalized biomarker model that satisfies the likelihood threshold.

11. The model-assisted system of claim 10, wherein the at least one processor is further programmed to access a database from which information associated with a population of individuals can be derived and wherein the generalized biomarker is configured to generate the output based on analyzing the information in association with the first biomarker.

12. The model-assisted system of claim 11, wherein the information includes a plurality of patient medical records associated with the population of individuals.

13. A computer-implemented method for identifying a group of individuals for a cohort using a generalized biomarker model, the method comprising:
    accessing a database from which information associated with a plurality of individuals can be derived, wherein the information includes a plurality of patient medical records associated with the plurality of individuals;
    providing, to the generalized biomarker model, a first biomarker associated with a cohort, the generalized biomarker model being trained based on one or more second biomarkers to detect one or more documents associated with representations of the first biomarker or biomarker testing, wherein the first biomarker is different from the one or more second biomarkers;

receiving, from the generalized biomarker model, an output indicating likelihoods, associated with the plurality of individuals, of at least one of: having an attribute associated with the first biomarker or having been tested for the attribute associated with the first biomarker;

determining a likelihood threshold based on a predetermined cohort size associated with the first biomarker; and identifying, based on the output, a group of the plurality of individuals for inclusion in the cohort, each individual in the group of the plurality of individuals being associated with a likelihood received from the generalized biomarker model that satisfies the likelihood threshold.

14. The computer-implemented method of claim 13, wherein the likelihood threshold is further determined based on a relative prevalence of the first biomarker.

15. The computer-implemented method of claim 13, wherein the likelihood threshold is further determined based on a relative ability of a healthcare provider to perform an action based on the first biomarker.

16. The computer-implemented method of claim 13, wherein the likelihood threshold is further determined based on a likelihood the cohort will be filled over the course of a particular study.

17. The computer-implemented method of claim 13, wherein the method further comprises training the generalized biomarker model based on the one or more second biomarkers.

18. The computer-implemented method of claim 17, wherein training the generalized biomarker includes:
identifying representations of the one or more second biomarkers in a plurality of training medical records;
extracting snippets of text surrounding the representations of the one or more second biomarkers;
generating a plurality of feature vectors based on the snippets; and
training the generalized biomarker model to detect documents associated with the one or more second biomarkers based on the plurality of feature vectors.

19. The computer-implemented method of claim 17, wherein training the generalized biomarker model to detect documents associated with the one or more second biomarkers includes applying a logistic regression algorithm.

20. A non-transitory computer-readable medium comprising instructions that, when executed by one or more processors, cause the one or more processors to perform a method for identifying a group of individuals for a cohort using a generalized biomarker model, the method comprising:

accessing a database from which information associated with a plurality of individuals can be derived, wherein the information includes a plurality of patient medical records associated with the plurality of individuals;

providing, to the generalized biomarker model, a first biomarker associated with a cohort, the generalized biomarker model being trained based on one or more second biomarkers to detect one or more documents associated with representations of the first biomarker or biomarker testing, wherein the first biomarker is different from the one or more second biomarkers;

receiving, from the generalized biomarker model, an output indicating likelihoods, associated with the plurality of individuals, of at least one of: having an attribute associated with the first biomarker or having been tested for an attribute associated with the first biomarker;

determining a likelihood threshold based on a predetermined cohort size associated with the first biomarker; and identifying, based on the output, a group of the plurality of individuals for inclusion in the cohort, each individual in the group of the plurality of individuals being associated with a likelihood received from the generalized biomarker model that satisfies the likelihood threshold.

* * * * *